(12) United States Patent
Hirschmann et al.

(10) Patent No.: US 7,255,811 B2
(45) Date of Patent: Aug. 14, 2007

(54) TOLANE DERIVATIVES AND LIQUID CRYSTALLINE MEDIUM

(75) Inventors: Harald Hirschmann, Darmstadt (DE);
Kevin Adlem, Bournemouth (GB);
Patricia Saxton, Hampshire (GB);
Mark John Goulding, Hampshire (GB); Martin Heeney, Southampton (GB)

(73) Assignee: Merck Patent GmbH, Darmstadt (DE)

( * ) Notice: Subject to any disclaimer, the term of this patent is extended or adjusted under 35 U.S.C. 154(b) by 623 days.

(21) Appl. No.: 10/848,385

(22) Filed: May 19, 2004

(65) Prior Publication Data

US 2004/0236138 A1 Nov. 25, 2004

(30) Foreign Application Priority Data

May 21, 2003 (EP) .................... 03011476

(51) Int. Cl.
*C09K 19/52* (2006.01)
*C09K 19/06* (2006.01)
*C07C 255/50* (2006.01)

(52) U.S. Cl. .............. 252/299.01; 252/299.6; 349/1; 349/192; 558/411

(58) Field of Classification Search .......... 252/299.01, 252/299.6; 349/1, 192; 558/411
See application file for complete search history.

(56) References Cited

U.S. PATENT DOCUMENTS

| | | | |
|---|---|---|---|
| 5,242,618 A | 9/1993 | Krause et al. | |
| 5,314,640 A | 5/1994 | Yamada | |
| 5,356,562 A | 10/1994 | Greenfield et al. | |
| 5,453,864 A | 9/1995 | Yamada et al. | |
| 5,658,489 A | 8/1997 | Higashii et al. | |

FOREIGN PATENT DOCUMENTS

| | | |
|---|---|---|
| DE | 41 11 990 | 10/1991 |
| EP | 0 442 266 | 8/1991 |
| EP | 0 648 723 | 4/1995 |
| WO | WO 92/18448 | 10/1992 |

OTHER PUBLICATIONS

Partial European Search Report dated Aug. 17, 2004.
S. Greenfield et al., "Laterally Fluorinated Tolanes of Low Melting Point", Liquid Crystals, Taylor and Francis Ltd., London, vol. 13, No. 2, (1993), pp. 301-305.

*Primary Examiner*—Johann Richter
*Assistant Examiner*—Ebenezer Sackey
(74) *Attorney, Agent, or Firm*—Millen, White, Zelano & Branigan, P.C.

(57) ABSTRACT

Tolane compounds of the formula I

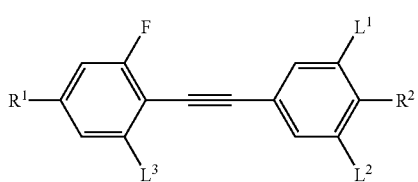

wherein $R^1$, $R^2$, $L^1$, $L^2$ and $L^3$ are as defined herein, are described. Further described are liquid-crystalline media comprising at least one tolane compound of formula I as well as liquid-crystal display elements containing such a liquid-crystalline medium.

20 Claims, No Drawings

TOLANE DERIVATIVES AND LIQUID CRYSTALLINE MEDIUM

The present invention relates to tolane compounds and derivatives and to liquid crystalline media containing at least one of these tolane compounds or derivatives. In addition the present invention relates to a liquid-crystal display element and to an electro-optical display element containing this liquid crystalline medium.

There exists an increasing demand for stable liquid crystalline compounds of a positive or negative value of the dielectric anisotropy and of a low rotational viscosity which can be used as components of liquid-crystalline media, in particular for displays based on the principle of the twisted cell, the guest-host effect, the effect of deformation of aligned phases (DAP) or electrically controlled birefringence (ECB) or the effect of dynamic scattering. Liquid crystals comprising an ester group have been used in liquid crystal displays (LCD), especially in active matrix LCDs, like for example thin film transistor (TFT) LCDs. Liquid crystalline media comprising such ester compounds enable advantageous low operating voltages, but their low stability against UV light restricts their use. Thus the use of such displays under intense UV radiation, like outdoor usage or in projection displays, leads to a decomposition of liquid crystals, which causes a decrease of the resistivity of the LC medium. The lower resistivity results in a lower contrast and therefore a shortened lifetime of the display.

Thus, there continues to be a great demand for liquid crystalline compounds, which are stable against radiation and enable low operating voltages in LCDs, in particular in displays based on a birefringence effect, such as ECB displays, and TFT-displays for outdoor usage. LC compounds are desired which have a very high resistivity at the same time as a wide operating temperature range, short response times and low threshold voltage, with the aid of which various grey shades can be produced. Furthermore, there is a great demand for liquid crystalline media for these kind of displays, which exhibit at the same time low viscosities, high birefringence, relatively high positive dielectric anisotropy and a high UV stability.

The invention has a first object to provide a compound, which exhibits a high UV stability and a relatively low rotational viscosity, which is therefore especially suitable as a component of liquid crystalline media in liquid-crystal displays.

A second object of the invention is a liquid crystalline medium, which overcomes the disadvantages mentioned above, at least in part, and at the same time shows a good UV stability.

Furthermore, the invention has a third object of providing a liquid crystal display element and an electro-optical display element, in particular an active matrix display, which does not have the above mentioned disadvantages, or does so only to a reduced extent.

Other aims and objects of the present invention are immediately evident to the person skilled in the art from the following detailed description.

The invention includes providing tolane compounds of the formula I

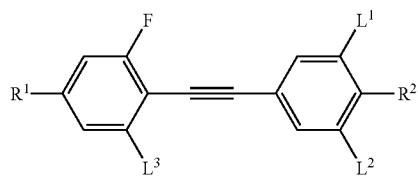

wherein
$R^1$ is an alkenyl group with 2 to 12 C-atoms,
$R^2$ is H, Halogen, CN, alkyl with 1 to 12 C-atoms, wherein one or more $CH_2$— groups may be replaced by —O—, —S—, —CO—, —O—CO—, —CO—O—, —CH=CH— and/or —C≡C—, and/or wherein one or more H-atoms may be replaced by halogen,
$L^1$, $L^2$ and $L^3$ are independently of each other H or F, but with the proviso that if $L^3$=H then $L^1$ and $L^2$=F.

The present invention thus includes a liquid crystalline compound of the formula I as defined above and below.

The compounds of the formula I preferably exhibit
a high UV stability,
a low affinity for ionic impurities,
a low rotational viscosity,
no tendency or at least a reduced tendency to form smectic phases,
a nematogenic behavior,
a low melting point.

In addition the compounds of the formula I show advantageous properties of the birefringence and of the dielectric anisotropy. In general they are nematogenic compounds for liquid-crystalline media with a low melting point and a good low temperature stability.

Because of these described advantageous properties, compounds of the formula I are especially suited as components of liquid crystalline media. Using one or more of these compounds in liquid crystalline media a high UV stability can be achieved. The low affinity for ionic impurities enables obtaining a high voltage holding ratio (VHR).

The provision of compounds of the formula I very generally considerably broadens the range of nematogenic substances which are suitable, from various applicational points of view, for the preparation of liquid-crystalline mixtures.

The compounds of the formula I have a broad range of applications. Depending on the choice of substituents, these compounds are preferably added to liquid-crystalline base materials from the same and/or other classes of compounds in order, for example, to modify the dielectric and/or optical anisotropy of a dielectric of this type and/or to optimize its threshold voltage and/or its viscosity. The compounds of the formula I may also serve as a component of base materials of liquid-crystalline media.

Therefore the invention also includes a liquid-crystalline medium having at least two liquid-crystalline components, which comprises at least one compound of the formula I.

Therefore, the present invention includes a liquid-crystalline medium having at least two liquid-crystalline components, which comprises at least one compound of the formula I.

Using one or more tolane derivatives according to formula I as components, liquid crystalline media with a broad nematic phase range, a low rotational viscosity and a high UV stability can be obtained.

Furthermore the invention includes a liquid-crystal display element, preferably an electro-optical display element, which contains, as a dielectric, a liquid-crystalline medium according to the present invention.

Therefore, the present invention also relates to a liquid-crystal display element and an electro-optical display element, which contains, as a dielectric, a liquid-crystalline medium according to the present invention.

The low rotational viscosity of the compounds according to the present invention leads to short response times of a display containing such an inventive medium as a dielectric. In addition, low threshold voltages are achievable by media containing one or more of the inventive compounds, especially those with a high positive dielectric anisotropy. As the inventive compounds exhibit a good UV stability and low melting points, the display element according to the present invention is advantageously suited for mobile application and outdoor usage. In addition, when using the inventive liquid crystalline medium in an electro-optical display, it is possible to achieve small values of the response time, a low driving voltage, a satisfying grey scale performance, a wide viewing angle and a high contrast.

In the following, preferred derivatives of the compound of the formula I, which are also preferred components of the liquid crystalline medium according to the present invention are given. Thus, a preferred liquid crystalline medium according to the present invention contains one or more of the preferred compounds of the formula I as specified below.

The meaning of the formula I covers all isotopes of the chemical elements bound in the compounds of the formula I. In enantiomerically pure or enriched form, the compounds of the formula I are also suitable as chiral dopants and in general for producing chiral mesophases.

In the pure state, the compounds of the formula I are colorless. They are stable chemically, thermally and to light.

Above and below, $R^1$, $R^2$, $L^1$, $L^2$ and $L^3$ are as defined above, unless expressly stated otherwise.

The compounds of formula I are preferably selected from the group of sub-formulae I-1 to I-4:

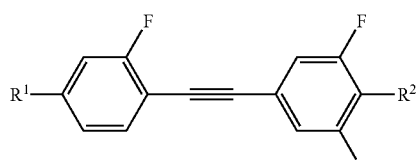

I-1

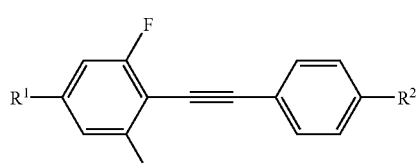

I-2

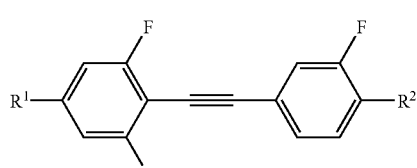

I-3

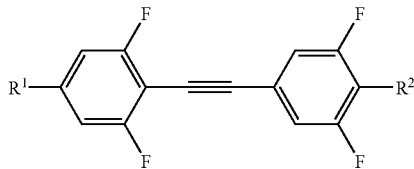

I-4 wherein $R^1$ and $R^2$ have the same meaning given with respect to formula I.

$R^1$ is an alkenyl group with 2 to 12 C-atoms. The term "alkenyl" comprises straight chain and branched alkenyl groups with 2 to 12 C atoms. Straight chain alkenyl groups with 2 to 8 C-atoms are preferred. Further preferred alkenyl groups are $C_2$-$C_8$-1E-alkenyl, $C_4$-$C_8$-3E-alkenyl, $C_5$-$C_8$-4-alkenyl, $C_6$-$C_8$-5-alkenyl, $C_7$-$C_8$-6-alkenyl and $C_8$-7-alkenyl, in particular $C_2$-$C_8$-1E-alkenyl, $C_4$-$C_8$-3E-alkenyl and $C_5$-$C_8$-4-alkenyl.

Of these, especially preferred alkenyl groups are vinyl, 1E-propenyl, 1E-butenyl, 1E-pentenyl, 1E-hexenyl, 1E-heptenyl, 1E-octenyl, 3-butenyl, 3E-pentenyl, 3E-hexenyl, 3E-heptenyl, 3E-octenyl, 4-pentenyl, 4Z-hexenyl, 4E-hexenyl, 4Z-heptenyl, 4E-octenyl, 5-hexenyl, 6-heptenyl and 7-octenyl. Alkenyl groups with 2 to 5 C atoms are particularly preferred.

$R^2$ is H, Halogen, CN, alkyl with 1 to 12 C-atoms, wherein one or more —$CH_2$-groups may be replaced by —O—, —S—, —CO—, —O—CO—, —CO—O—, —CH=CH— and/or —C≡C—, and/or wherein one or more H-atoms may be replaced by halogen.

Halogen is F, Cl, Br or I, preferably F or Cl and in particular F. In the case of polysubstitution, halogen is particularly F.

If $R^2$ is alkyl with 1 to 12 C-atoms, wherein one or more —$CH_2$-groups may be replaced by —O—, —S—, —CO—, —O—CO—, —CO—O—, —CH=CH— and/or —C≡C—, and/or wherein one or more H-atoms may be replaced by halogen, it is preferably alkyl, oxaalkyl or alkoxy with 1 to 8 C-atoms and/or alkenyl, alkenyloxy or oxaalkenyl with 2 to 8 C-atoms, wherein one or more H-atoms of the alkyl, alkoxy, oxaalkyl, alkenyl, alkenyloxy or oxaalkenyl groups may be replaced by F and/or Cl.

The term "alkyl" comprises straight chain and branched alkyl groups with 1 to 12 C-atoms. Straight chain alkyl groups with 1 to 8 C-atoms are preferred. Thus, preferred alkyl groups are methyl, ethyl, propyl, butyl, pentyl, hexyl, heptyl and octyl. Furthermore preferred are alkyl groups wherein one or more H-atoms are replaced by F. Examples of such preferred alkyl groups are: —$CHF_2$, —$CF_3$, —$CH_2CHF_2$, —$CH_2CF_3$, —$CF_2CHF_2$, —$CF_2CF_3$, —$CH_2CH_2CHF_2$, —$CH_2CH_2CF_3$, —$CH_2CF_2CHF_2$, —$CH_2CF_2CF_3$, —$CF_2CH_2CHF_2$, —$CF_2CH_2CF_3$, —$CF_2CF_2CHF_2$ and —$CF_2CF_2CF_3$.

The term "alkoxy" comprises straight chain and branched alkoxy groups with 1 to 12 C-atoms. Straight chain alkoxy groups with 1 to 8 C-atoms are preferred. Thus, preferred alkoxy groups are methoxy, ethoxy, propoxy, butoxy, pentoxy, hexoxy, heptoxy and octoxy. Furthermore preferred are alkoxy groups wherein one or more H-atoms are replaced by F. Examples of such preferred alkoxy groups are: —$OCHF_2$, —$OCF_3$, —$OCH_2CHF_2$, —$OCH_2CF_3$, —$OCF_2CHF_2$, —$OCF_2CF_3$, —$OCH_2CH_2CHF_2$, —$OCH_2CH_2CF_3$, —$OCH_2CF_2CHF_2$, —$OCH_2CF_2CF_3$, —$OCF_2CH_2CHF_2$, —$OCF_2CH_2CF_3$, —$OCF_2CF_2CHF_2$ and —$OCF_2CF_2CF_3$.

The term "alkenyl" comprises straight chain and branched alkenyl groups with 2 to 12 C atoms. Straight chain alkenyl groups with 2 to 8 C-atoms are preferred. Further preferred alkenyl groups are $C_2$-$C_8$-1E-alkenyl, $C_4$-$C_8$-3E-alkenyl, $C_5$-$C_8$-4-alkenyl, $C_6$-$C_8$-5-alkenyl, $C_7$-$C_8$-6-alkenyl and $C_8$-7-alkenyl, in particular $C_2$-$C_8$-1E-alkenyl, $C_4$-$C_8$-3E-alkenyl and $C_5$-$C_8$-4-alkenyl. Furthermore preferred are alkenyl groups wherein one or more H-atoms are replaced by F. Examples of such preferred alkenyl groups are: —CH=CHF, —CF=CH$_2$, —CF=CHF, —CH=CF$_2$, —CF=CF$_2$, —CH=CH—CF$_3$, —CH=CF—CF$_3$, —CF=CF—CF$_3$, —CH$_2$—CH=CHF, —CH$_2$—CH=CF$_2$, —CF$_2$—CH=CH$_2$, —CF$_2$—CH=CHF, —CF$_2$—CH=CF$_2$, —CF$_2$—CF=CF$_2$ and —CF$_2$—CF=CF—CF$_3$.

If $R^2$ is an alkenyloxy group, it is preferably selected from the group consisting of —OCH=CH$_2$, —OCH=CH—CH$_3$, —OCH$_2$—CH=CH$_2$, —OCH=CHF, —OCF=CH$_2$, —OCF=CHF, —OCH=CF$_2$, —OCF=CF$_2$, —OCH=CH—CF$_3$, —OCH=CF—CF$_3$, —OCF=CF—CF$_3$, —OCH$_2$—CH=CHF, —OCH$_2$—CH=CF$_2$, —OCH$_2$—CF=CF$_2$, —OCF$_2$—CH=CH$_2$, —OCF$_2$—CH=CHF, —OCF$_2$—CH=CF$_2$, —OCF$_2$—CF=CF$_2$, —OCH$_2$—CH=CH—CF$_3$, —OCF$_2$—CH=CH—CF$_3$, —OCF$_2$—CH=CH—CF$_3$ and —OCF$_2$—CF=CF—CF$_3$.

If $R^2$ is an oxaalkyl group, it is preferably selected from the group consisting of —CH$_2$OCH$_3$, —CH$_2$OC$_2$H$_5$, —CH$_2$OCHF$_2$, —CH$_2$OCF$_3$, —CF$_2$OCH$_3$, —CF$_2$OCHF$_2$, —CF$_2$OCF$_3$, —CH$_2$OCH$_2$CHF$_2$, —CH$_2$OCH$_2$CF$_3$, —CH$_2$OCF$_2$CF$_3$, —CF$_2$OCH$_2$CF$_3$ and —CF$_2$OCF$_2$CF$_3$.

If $R^2$ is an oxaalkenyl group, it is preferably selected from the group consisting of —CH$_2$OCH=CH$_2$, —CH$_2$OCH=CHF, —CH$_2$OCH=CF$_2$, —CH$_2$OCF=CF$_2$, —CF$_2$OCH=CH$_2$, —CF$_2$OCH=CHF, —CF$_2$OCH=CF$_2$, —CF$_2$OCF=CF$_2$ and —CH$_2$OCH=CH—CF$_3$.

Compounds of the formula I containing a branched wing group $R^2$ may occasionally be of importance owing to better solubility in the customary liquid-crystalline base materials, but in particular as chiral dopants if they are optically active. Smectic compounds of this type are suitable as components of ferroelectric materials.

Branched groups of this type generally contain not more than one chain branch. Preferred branched radicals $R^2$ are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentyloxy, 3-methylpentyloxy, 2-ethylhexyloxy, 1-methylhexyloxy and 1-methylheptyloxy.

Those inventive compounds of formula I are particularly preferred wherein $R^2$ is —F, —Cl, —CN, —H, —CH$_3$, —CHF$_2$, —CF$_3$, —OCH$_3$, —OCHF$_2$, —OCF$_3$, —CH=CH$_2$, —CH=CHF, —CH=CF$_2$, —CF=CH$_2$, —CF=CHF and —CF=CF$_2$. In particular, $R^2$ is —H, —F, —CN, —CHF$_2$, —CF$_3$, —OCH$_3$, —OCHF$_2$ and —OCF$_3$.

Preferred are those compounds according to the present invention which exhibit a positive dielectric anisotropy Δε, preferably Δε≧4, more preferably Δε≧10, and in particular Δε≧20.

Formula I covers the racemates of these compounds and the optical antipodes, and mixtures thereof.

Of these compounds of formula I and the sub-formulae, preference is given to those in which at least one of the radicals and/or substituents present therein has one of the preferred meanings indicated.

The compounds of the formula I are prepared using methods known to the person skilled in the art, as described in the literature (for example in the standard works, such as Houben-Weyl, *Methoden der Organischen Chemie*, Georg-Thieme Verlag Stuttgart) under reaction conditions which are known and suitable for said reactions. Use can be made of variants, which are known per se, but are not mentioned here in greater detail. The starting materials can, if desired, also be formed in situ by not isolating them from the reaction mixture, but instead immediately converting them further into the compounds of formula I.

The compounds according to the present invention can be prepared, for example, as shown in the following reaction scheme.

Reaction Scheme:

($L^1$, $L^2$, $L^3$=independently of each other H or F, Hal=I or Br)

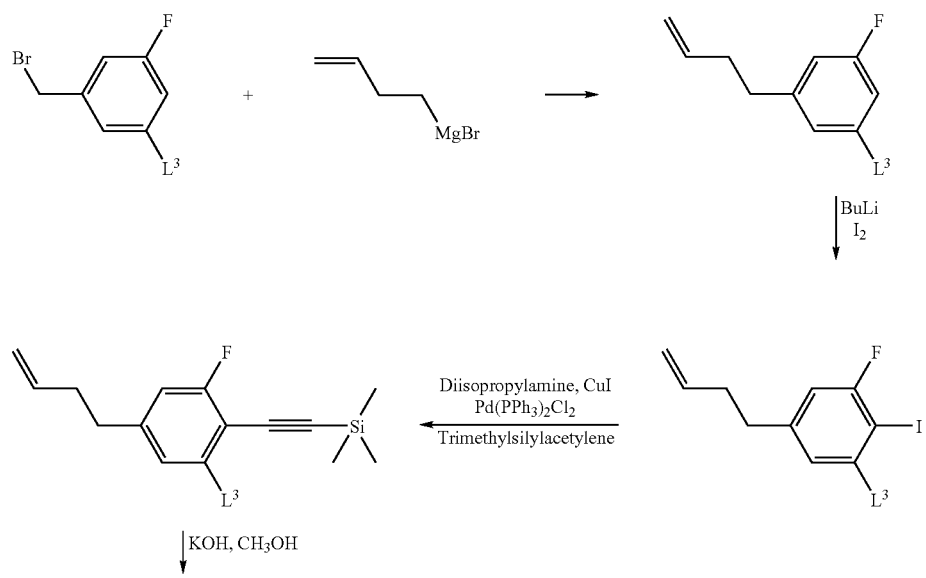

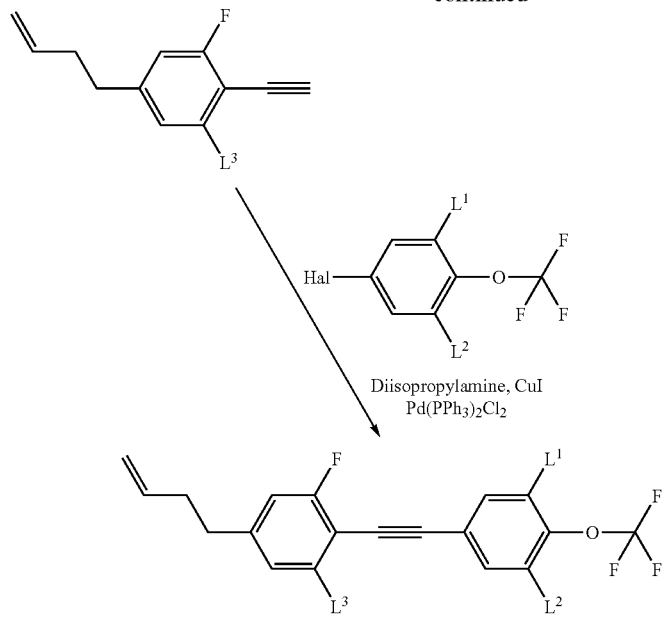

The starting materials are either known or can be prepared analogously to known compounds.

The liquid-crystalline media according to the present invention preferably comprise from 2 to 40 components, more preferably from 4 to 30 components, as further constituents besides one or more compounds according to the present invention. These media in particular comprise from 7 to 25 components besides one or more compounds according to the present invention. These further constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl cyclohexanecarboxylates, phenyl or cyclohexyl cyclohexylbenzoates, phenyl or cyclohexyl cyclohexylcyclohexanecarboxylates, cyclohexylphenyl benzoates, cyclohexanecarboxylates and cyclohexylcyclohexanecar-boxylates, phenylcyclohexanes, cyclohexylbiphenyls, phenylcyclohexyl-cyclohexanes, cyclohexylcyclohexanes, cyclohexylcyclohexylcyclohexenes, 1,4-bis-cyclohexylbenzenes, 4,4'-bis-cyclohexylbiphenyls, phenyl- or cyclohexylpyrimidines, phenyl- or cyclohexylpyridines, phenyl- or cyclo-hexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylylethanes, 1-phenyl-2-cyclohexylphenylethanes optionally halogenated stilbenes, benzyl phenyl ethers, tolans and substituted cinnamic acids. The 1,4-phenylene groups in these compounds may also be fluorinated.

The most preferred compounds suitable as further constituents of media according to the present invention can be characterized by the formulae 1, 2, 3, 4 and 5:

| | |
|---|---|
| R'-L-E-R" | 1 |
| R'-L-COO-E-R" | 2 |
| R'-L-OOC-E-R" | 3 |
| R'-L-CH$_2$CH$_2$-E-R" | 4 |
| R'-L-C≡C-E-R" | 5 |

In the formulae 1, 2, 3, 4 and 5, L and E, which may be identical or different, are in each case, independently of one another, a bivalent radical from the group formed by -Phe-, -Cyc-, -Phe-Phe-, -Phe-Cyc-, -Cyc-Cyc-, -Pyr-, -Dio-, -G-Phe- and -G-Cyc- and their mirror images, where Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl and G is 2-(trans-1,4-cyclohexyl)ethyl.

One of the radicals L and E is preferably Cyc, Phe or Pyr. E is preferably Cyc, Phe or Phe-Cyc. The media according to the present invention preferably comprise one or more components selected from the compounds of the formulae 1, 2, 3, 4 and 5 in which L and E are selected from the group consisting of Cyc, Phe and Pyr and simultaneously one or more components selected from the compounds of the formulae 1, 2, 3, 4 and 5 in which one of the radicals L and E is selected from the group consisting of Cyc, Phe and Pyr and the other radical is selected from the group consisting of -Phe-Phe-, -Phe-Cyc-, -Cyc-Cyc-, -G-Phe- and -G-Cyc-, and optionally one or more components selected from the compounds of the formulae 1, 2, 3, 4 and 5 in which the radicals L and E are selected from the group consisting of -Phe-Cyc-, -Cyc-Cyc-, -G-Phe- and -G-Cyc-.

In a smaller sub-group of the compounds of the formulae 1, 2, 3, 4 and 5, R' and R" are each, independently of one another, alkyl, alkenyl, alkoxy, alkoxyalkyl, alkenyloxy or alkanoyloxy having up to 8 carbon atoms. This smaller sub-group is called group A below, and the compounds are denoted by the sub-formulae 1a, 2a, 3a, 4a and 5a. In most of these compounds, R' and R" are different from one another, one of these radicals usually being alkyl, alkenyl, alkoxy or alkoxyalkyl.

In another smaller sub-group of the compounds of the formulae 1, 2, 3, 4 and 5, which is called group B, R" is —F, —Cl, —NCS or —(O)$_t$CH$_{3-(k+1)}$F$_k$Cl$_1$, where i is 0 or 1, and k and 1 are 1, 2 or 3; the compounds in which R" has this meaning are denoted by the sub-formulae 1b, 2b, 3b, 4b and 5b. Particular preference is given to those compounds of the sub-formulae 1b, 2b, 3b, 4b and 5b in which R" is —F, —Cl, —NCS, —CF$_3$, —OCHF$_2$ or —OCF$_3$.

In the compounds of the sub-formulae 1b, 2b, 3b, 4b and 5b, R' is as defined for the compounds of the sub-formulae 1a to 5a and is preferably alkyl, alkenyl, alkoxy or alkoxyalkyl.

In a further smaller sub-group of the compounds of the formulae 1, 2, 3, 4 and 5, R" is —CN; this sub-group is called group C below, and the compounds of this sub-group are correspondingly described by sub-formulae 1c, 2c, 3c, 4c and 5c. In the compounds of the sub-formulae 1c, 2c, 3c, 4c and 5c, R' is as defined for the compounds of the sub-formulae 1a to 5a and is preferably alkyl, alkoxy or alkenyl.

In addition to the preferred compounds of groups A, B and C, other compounds of the formulae 1, 2, 3, 4 and 5 having other variants of the proposed substituents are also customary. All these substances can be obtained by methods, which are known from the literature or analogously thereto.

Besides compounds of the formula I according to the present invention, the media according to the present invention preferably comprise one or more compounds selected from group A, B and/or C. The proportions by weight of the compounds from these groups in the media according to the present invention are preferably:

Group A: 0 to 90%, preferably 20 to 90%, in particular 30 to 90%

Group B: 0 to 80%, preferably 10 to 80%, in particular 10 to 65%

Group C: 0 to 80%, preferably 5 to 80%, in particular 5 to 50%, the sum of the proportions by weight of the group A, B and/or C compounds present in the particular media according to the present invention preferably being 5% to 90% and in particular from 10% to 90%.

The media according to the present invention preferably comprise from 1 to 40%, more preferably from 5 to 30%, of the compounds of formula I according to the present invention. The media may also comprise more than 40% of compounds according to formula I of the present invention. The media preferably comprise three, four or five compounds according to formula I of the present invention.

In addition the media may contain one or more additives, like e.g. chiral dopants, antioxidants and/or UV stabilizers. Suitable derivatives of such additives and their amount within the media are known to the one skilled in the art.

The media according to the present invention are prepared in a manner, which is customary per se. In general, the components are dissolved in one another, advantageously at elevated temperature. By means of suitable additives, the liquid-crystalline phases can be modified in accordance with the present invention in such a manner that they can be used in all types of liquid-crystal display elements, which have been disclosed hitherto. Additives of this type are known to those skilled in the art and are described in detail in the literature (H. Kelker/R. Hatz, *Handbook of Liquid Crystals*, Verlag Chemie, Weinheim, 1980). For example, pleochroic dyes can be added for the production of colored guest-host systems, or substances can be added to modify the dielectric anisotropy, the viscosity and/or the orientation of the nematic phases.

The liquid-crystalline medium according to the present invention is advantageously suitable for displays based on the principle of the twisted cell, the guest-host effect, the effect of deformation of aligned phases DAP or ECB (electrically controlled birefringence), the IPS (in-plane switching) effect or the effect of dynamic scattering, in particular for TN, STN, IPS and TFT displays. Accordingly the present invention also relates to such a liquid-crystal display element and/or electro-optical display element comprising an inventive liquid-crystalline medium.

The entire disclosure of all applications, patents and publications, cited herein and of corresponding European application No. 03011476.3, filed May 21, 2003, is incorporated by reference herein.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

The examples below are intended to illustrate the invention without representing a limitation. Above and below, percentages are percent by weight. All temperatures are given in degrees Celsius. m.p. denotes melting point and cl.p.=clearing point. Furthermore, C=crystalline state, N=nematic phase, Sm=smectic phase and I=isotropic phase. The numbers between these symbols indicate the conversion temperatures. Δn denotes the optical anisotropy (589 nm, 20° C.) and Δε the dielectric anisotropy (1 kHz, 20° C.). The Δn and Δε values of the compounds according to the invention were obtained by extrapolation from liquid-crystalline mixtures consisting of 10% of the particular compound according to the invention and 90% of the commercially available liquid crystal ZLI 4792 (Merck, Darmstadt).

The displays are addressed with squarewave voltage of frequency 80 Hz at 20° C. The characteristic voltages have been determined under perpendicular observation. The term threshold voltage refers in the instant application to the optical threshold and is given for 10% relative contrast ($V_{10}$) and the term saturation voltage refers to the optical saturation and is given for 90% relative contrast ($V_{90}$), both if not explicitly stated otherwise.

The response times have been determined with simulated time sequential addressing, also called "multiplex addressing", with respective duty ratio and bias ratio at 20° C. The response time for switching on $t_{on}$ has been determined for the time from the change of the addressing voltage from the "off" level to the "on" level up to 90% of relative contrast, whereas the time for switching off $t_{off}$ has been determined for the opposite change of voltage to 10% of relative contrast, i.e. both are including a possible delay time. The average response time $t_{ave}$, i.e. the average of $t_{on}$ and $t_{off}$ is given for the operation voltage at which the lowest average response time is observed.

"Conventional work-up" means that water is added if necessary, the mixture is extracted with methylene chloride, diethyl ether or toluene, the phases are separated, the organic phase is dried and evaporated, and the product is purified by distillation under reduced pressure or crystallization and/or chromatography.

EXAMPLE 1

Preparation of the tolane compound of the following formula:

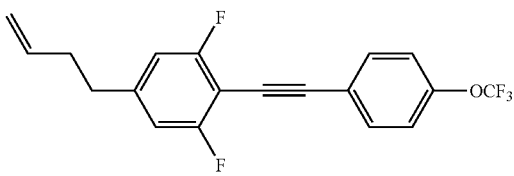

1.1 Preparation of 1,3 difluoro-5-(3-butenyl)-benzene

To a dry, round bottom flask was charged 0.43 mol 3,5-difluorobenzyl-bromide and 300 ml anhydrous tetrahydrofuran. The mixture was cooled under nitrogen atmosphere to 0° C. at which time a solution of 0.54 mol allylmagnesiumchloride in 270 ml tetrahydrofuran was slowly added keeping the temperature at 0° C. After allowing to warm to room temperature and stirring until completion (20 hours), the reaction was quenched with an excess of diluted hydrochloric acid. The organic layer was separated, and the aqueous layer extracted twice with petroleum spirits (2×75 ml). The organic layers were combined, washed with water (2×75 ml) and dried over anhydrous sodium sulphate. Removal of the solvent yielded 68 g of the title compound as a pale oil.

1.2 Preparation of 1,3-difluoro-2-iodo-5-(3-butenyl)-benzene 0.41 mol 1,3 difluoro-5-(3-butenyl)-benzene was added to a dry round bottom flask with 300 ml anhydrous tetrahydrofuran. After cooling under a nitrogen atmosphere to −70° C. a solution of 0.46 mol of n-butyllithium in 280 ml hexane was added. After stirring at −70° C. for 30 minutes a mixture of 0.46 mol of Iodine in 200 ml tetrahydrofuran was added slowly over 2 hours. The reaction was left to warm to room temperature overnight. The reaction was quenched by pouring onto ice/hydrochloric acid mixture. The layers were separated and the aqueous layer extracted twice with diethyl ether (2×100 ml). The combined organic layers were washed with 50 g sodium thiosulphate in 200 ml water to remove excess iodine, then with water (2×50 ml) and dried over anhydrous sodium sulphate. Removal of the solvent yielded 126 g of the title compound as a beige solid.

1.3 Preparation of 1,3-difluoro-2-trimethylsilylacetylyl-5-(3-butenyl)-benzene To a dry 3 necked flask was added 0.356 mol of 1,3-difluoro-2-iodo-5-(3-butenyl)-benzene, 0.011 mol copper (I) Iodide and 0.004 mol bis(triphenylphosphine)-palladium (II) dichloride. The flask was evacuated and backfilled with nitrogen three times. 150 ml of diethylamine was added via a syringe, and the whole reaction stirred and cooled to 5° C. 0.356 mol of trimethylsilyl acetylene was added via syringe over 10 minutes and the reaction stirred for 1 hour, after which it was heated to 50° C. for 24 hours. The reaction was allowed to cool and any precipitated solids were washed onto and through a filter using tetrahydrofuran. The filtrate was concentrated under reduced pressure to afford 72 g of the target material.

1.4 Preparation of 1,3-difluoro-2-acetylyl-5-(3-butenyl)-benzene

To a dry flask was added 0.076 mol of 1,3-difluoro-2-trimethylsilylacetylyl-5-(3-butenyl)-benzene, 100 ml tetrahydrofuran and 50 ml methanol. The flask was evacuated and backfilled with nitrogen three times after which it was cooled to −40° C. A solution of 0.076 mol of potassium hydroxide in 12 ml water was added slowly. The reaction was allowed to warm to room temperature and stirred for a further two hours. 25 ml water and 50 ml diethyl ether were added and the layers partitioned. Extraction of the aqueous phase with ether (2×50 ml) was followed by washing of the combined organic layers with diluted hydrochloric acid. Washing with water until pH=7 was required and concentration after drying over anhydrous sodium sulphate gave 7 g of the target material.

1.5 Preparation of 2.6-difluoro-4-(3-butenyl)-4'-trifluoromethoxy-tolane

To a dry 3 necked flask was added 0.63 mmol copper (I) iodide, 0.44 mmol bis(triphenylphosphine)-palladium (II) dichloride, 100 ml diethylamine and 21 mmol 4-iodo-(trifluoromethoxy)benzene. The flask was evacuated and backfilled with nitrogen three times before being cooled to −10° C. 21 mmol 1,3-difluoro-2-acetylyl-5-(3-butenyl)-benzene was slowly added with vigorous stirring and the whole left at −10° C. for 30 minutes. After warming to room temperature the reaction was heated to 60° C. for 72 hours. The reaction was allowed to cool and any precipitated solids were washed onto and through a filter using dichloromethane. The filtrate was concentrated under reduced pressure to afford the crude target material. Following purification by column chromatography using petroleum spirits, the material was recrystallized from petrol to yield the final material in high purity (100% GC).

The compound has the following properties:

K 30.6 I $\Delta\epsilon=10.3$ $\Delta n=0.1949$

EXAMPLES 2 TO 42

The compounds of the following formula are prepared by procedures similar to the procedure of example 1

| example | $R^1$ | m | $R^2$ |
|---|---|---|---|
| 2 | H | 0 | F |
| 3 | H | 0 | CN |
| 4 | H | 0 | $CHF_2$ |
| 5 | H | 0 | $CF_3$ |
| 6 | H | 0 | $OCHF_2$ |
| 7 | H | 0 | $OCF_3$ |
| 8 | $CH_3$ | 0 | F |
| 9 | $CH_3$ | 0 | CN |
| 10 | $CH_3$ | 0 | $CHF_2$ |
| 11 | $CH_3$ | 0 | $CF_3$ |
| 12 | $CH_3$ | 0 | $OCHF_2$ |
| 13 | $CH_3$ | 0 | $OCF_3$ |
| 14 | $C_2H_5$ | 0 | F |
| 15 | $C_2H_5$ | 0 | CN |
| 16 | $C_2H_5$ | 0 | $CHF_2$ |
| 17 | $C_2H_5$ | 0 | $CF_3$ |
| 18 | $C_2H_5$ | 0 | $OCHF_2$ |
| 19 | $C_2H_5$ | 0 | $OCF_3$ |

-continued

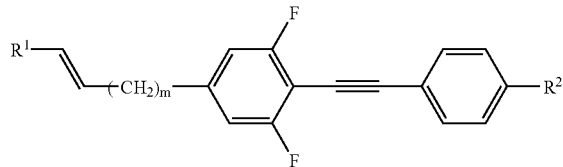

| example | R¹ | m | R² |
|---|---|---|---|
| 20 | C₃H₇ | 0 | F |
| 21 | C₃H₇ | 0 | CN |
| 22 | C₃H₇ | 0 | CHF₂ |
| 23 | C₃H₇ | 0 | CF₃ |
| 24 | C₃H₇ | 0 | OCHF₂ |
| 25 | C₃H₇ | 0 | OCF₃ |
| 26 | H | 2 | F |
| 27 | H | 2 | CN |
| 28 | H | 2 | CHF₂ |
| 29 | H | 2 | CF₃ |
| 30 | H | 2 | OCHF₂ |
| 31 | CH₃ | 2 | F |
| 32 | CH₃ | 2 | CN |
| 33 | CH₃ | 2 | CHF₂ |
| 34 | CH₃ | 2 | CF₃ |
| 35 | CH₃ | 2 | OCHF₂ |
| 36 | CH₃ | 2 | OCF₃ |
| 37 | H | 3 | F |
| 38 | H | 3 | CN |
| 39 | H | 3 | CHF₂ |
| 40 | H | 3 | CF₃ |
| 41 | H | 3 | OCHF₂ |
| 42 | H | 3 | OCF₃ |

EXAMPLES 43 TO 84

The compounds of the following formula are prepared by procedures similar to the procedure of example 1 and/or as described in the reaction scheme.

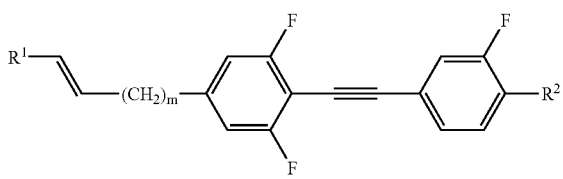

| example | R¹ | m | R² |
|---|---|---|---|
| 43 | H | 0 | F |
| 44 | H | 0 | CN |
| 45 | H | 0 | CHF₂ |
| 46 | H | 0 | CF₃ |
| 47 | H | 0 | OCHF₂ |
| 48 | H | 0 | OCF₃ |
| 49 | CH₃ | 0 | F |
| 50 | CH₃ | 0 | CN |
| 51 | CH₃ | 0 | CHF₂ |
| 52 | CH₃ | 0 | CF₃ |
| 53 | CH₃ | 0 | OCHF₂ |
| 54 | CH₃ | 0 | OCF₃ |
| 55 | C₂H₅ | 0 | F |
| 56 | C₂H₅ | 0 | CN |
| 57 | C₂H₅ | 0 | CHF₂ |
| 58 | C₂H₅ | 0 | CF₃ |
| 59 | C₂H₅ | 0 | OCHF₂ |
| 60 | C₂H₅ | 0 | OCF₃ |
| 61 | C₃H₇ | 0 | F |
| 62 | C₃H₇ | 0 | CN |
| 63 | C₃H₇ | 0 | CHF₂ |

-continued

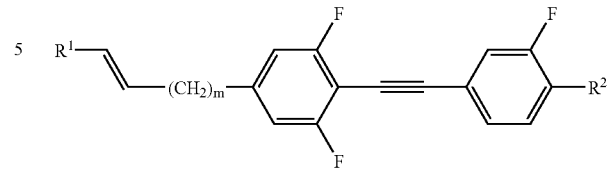

| example | R¹ | m | R² |
|---|---|---|---|
| 64 | C₃H₇ | 0 | CF₃ |
| 65 | C₃H₇ | 0 | OCHF₂ |
| 66 | C₃H₇ | 0 | OCF₃ |
| 67 | H | 2 | F |
| 68 | H | 2 | CN |
| 69 | H | 2 | CHF₂ |
| 70 | H | 2 | CF₃ |
| 71 | H | 2 | OCHF₂ |
| 72 | H | 2 | OCF₃ |
| 73 | CH₃ | 2 | F |
| 74 | CH₃ | 2 | CN |
| 75 | CH₃ | 2 | CHF₂ |
| 76 | CH₃ | 2 | CF₃ |
| 77 | CH₃ | 2 | OCHF₂ |
| 78 | CH₃ | 2 | OCF₃ |
| 79 | H | 3 | F |
| 80 | H | 3 | CN |
| 81 | H | 3 | CHF₂ |
| 82 | H | 3 | CF₃ |
| 83 | H | 3 | OCHF₂ |
| 84 | H | 3 | OCF₃ |

EXAMPLE 85

Preparation of the tolane compound of the following formula:

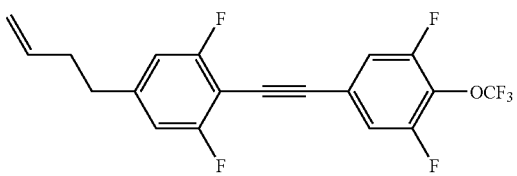

Preparation of 2,6-difluoro-4-(3-butenyl)-3,5-difluoro-4'-trifluoromethoxy-tolane To a dry 3 necked flask was added 0.63 mmol copper (I) iodide, 0.44 mmol bis(triphenylphosphine)-palladium (II) dichloride, 100 ml diethylamine and 21 mmol 2,6-difluoro-4-iodo-(trifluoromethoxy)benzene. The flask was evacuated and backfilled with nitrogen three times before being cooled to −10° C. 21 mmol 1,3-difluoro-2-acetylyl-5-(3-butenyl)-benzene was added slowly with vigorous stirring and the whole left at −10° C. for 30 minutes. After warming to room temperature the reaction was heated to 60° C. for 72 hours. The reaction was allowed to cool and any precipitated solids were washed onto and through a filter using dichloromethane. The filtrate was concentrated under reduced pressure to afford the crude target material. Following purification by column chromatography using petroleum spirits, the material was recrystallized from petrol to yield the final material in high purity (100% GC).

The compound has the following properties:

K 54.7 I $\Delta\epsilon = 18.6$ $\Delta n = 0.1456$

EXAMPLE 86

Preparation of the tolane compound of the following formula:

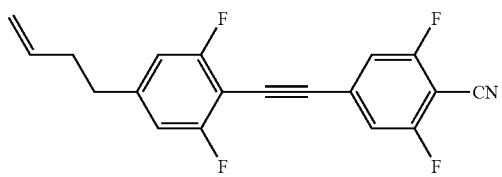

Preparation of 2,6-difluoro-4-(3-butenyl)-3,5-difluoro-4'-cyano-tolane

To a dry 3 necked flask was added 1.04 mmol copper (I) iodide, 0.52 mmol bis(triphenylphosphine)-palladium (II) dichloride, 20 ml dimethylformamide, 5.22 mmol 1,1,1-Trifluoro-methanesulfonic acid 4-cyano-3,5-difluoro-phenyl ester and 5.22 mmol (4-But-3-enyl-2,6-difluoro-phenylethynyl)-trifluoro-silane. The flask was evacuated and backfilled with nitrogen three times before being heated to 80° C. for 24 hours. The reaction was allowed to cool and diluted with 10 ml water. The material was extracted three times with 20 ml dichloromethane and the combined extractions dried over anhydrous sodium sulphate before removing the solvent under reduced pressure to afford the target material. Purification by column chromatography using toluene yielded the pure material in high yield (>97% GC).

The compound has the following properties:
K 97.2 I
Δε=43.8
Δn=0.2173

EXAMPLES 87 to 126

The compounds of the following formula are prepared by procedures similar to the procedures of examples 85 and 86.

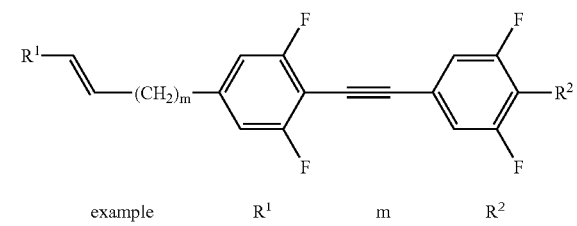

| example | $R^1$ | m | $R^2$ |
|---|---|---|---|
| 87 | H | 0 | F |
| 88 | H | 0 | CN |
| 89 | H | 0 | $CHF_2$ |
| 90 | H | 0 | $CF_3$ |
| 91 | H | 0 | $OCHF_2$ |
| 92 | H | 0 | $OCF_3$ |
| 93 | $CH_3$ | 0 | F |
| 94 | $CH_3$ | 0 | CN |
| 95 | $CH_3$ | 0 | $CHF_2$ |
| 96 | $CH_3$ | 0 | $CF_3$ |
| 97 | $CH_3$ | 0 | $OCHF_2$ |
| 98 | $CH_3$ | 0 | $OCF_3$ |
| 99 | $C_2H_5$ | 0 | F |
| 100 | $C_2H_5$ | 0 | CN |
| 101 | $C_2H_5$ | 0 | $CHF_2$ |
| 102 | $C_2H_5$ | 0 | $CF_3$ |
| 103 | $C_2H_5$ | 0 | $OCHF_2$ |
| 104 | $C_2H_5$ | 0 | $OCF_3$ |
| 105 | $C_3H_7$ | 0 | F |
| 106 | $C_3H_7$ | 0 | CN |
| 107 | $C_3H_7$ | 0 | $CHF_2$ |
| 108 | $C_3H_7$ | 0 | $CF_3$ |
| 109 | $C_3H_7$ | 0 | $OCHF_2$ |
| 110 | $C_3H_7$ | 0 | $OCF_3$ |
| 111 | H | 2 | F |
| 112 | H | 2 | $CHF_2$ |
| 113 | H | 2 | $CF_3$ |
| 114 | H | 2 | $OCHF_2$ |
| 115 | $CH_3$ | 2 | F |
| 116 | $CH_3$ | 2 | CN |
| 117 | $CH_3$ | 2 | $CHF_2$ |
| 118 | $CH_3$ | 2 | $CF_3$ |
| 119 | $CH_3$ | 2 | $OCHF_2$ |
| 120 | $CH_3$ | 2 | $OCF_3$ |
| 121 | H | 3 | F |
| 122 | H | 3 | CN |
| 123 | H | 3 | $CHF_2$ |
| 124 | H | 3 | $CF_3$ |
| 125 | H | 3 | $OCHF_2$ |
| 126 | H | 3 | $OCF_3$ |

EXAMPLES 127 TO 168

The compounds of the following formula are prepared by procedures similar to the procedures of the previous examples and/or as described in the reaction scheme.

| example | $R^1$ | m | $R^2$ |
|---|---|---|---|
| 127 | H | 0 | F |
| 128 | H | 0 | CN |
| 129 | H | 0 | $CHF_2$ |
| 130 | H | 0 | $CF_3$ |
| 131 | H | 0 | $OCHF_2$ |
| 132 | H | 0 | $OCF_3$ |
| 133 | $CH_3$ | 0 | F |
| 134 | $CH_3$ | 0 | CN |
| 135 | $CH_3$ | 0 | $CHF_2$ |
| 136 | $CH_3$ | 0 | $CF_3$ |
| 137 | $CH_3$ | 0 | $OCHF_2$ |
| 138 | $CH_3$ | 0 | $OCF_3$ |
| 139 | $C_2H_5$ | 0 | F |
| 140 | $C_2H_5$ | 0 | CN |
| 141 | $C_2H_5$ | 0 | $CHF_2$ |
| 142 | $C_2H_5$ | 0 | $CF_3$ |
| 143 | $C_2H_5$ | 0 | $OCHF_2$ |
| 144 | $C_2H_5$ | 0 | $OCF_3$ |
| 145 | $C_3H_7$ | 0 | F |
| 146 | $C_3H_7$ | 0 | CN |
| 147 | $C_3H_7$ | 0 | $CHF_2$ |
| 148 | $C_3H_7$ | 0 | $CF_3$ |

-continued

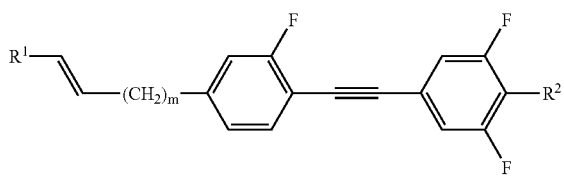

| example | R¹ | m | R² |
|---|---|---|---|
| 149 | C₃H₇ | 0 | OCHF₂ |
| 150 | C₃H₇ | 0 | OCF₃ |
| 151 | H | 2 | F |
| 152 | H | 2 | CN |
| 153 | H | 2 | CHF₂ |
| 154 | H | 2 | CF₃ |
| 155 | H | 2 | OCHF₂ |
| 156 | H | 2 | OCF₃ |
| 157 | CH₃ | 2 | F |
| 158 | CH₃ | 2 | CN |
| 159 | CH₃ | 2 | CHF₂ |
| 160 | CH₃ | 2 | CF₃ |
| 161 | CH₃ | 2 | OCHF₂ |
| 162 | CH₃ | 2 | OCF₃ |
| 163 | H | 3 | F |
| 164 | H | 3 | CN |
| 165 | H | 3 | CHF₂ |
| 166 | H | 3 | CF₃ |
| 167 | H | 3 | OCHF₂ |
| 168 | H | 3 | OCF₃ |

EXAMPLE 169

A mixture is prepared consisting of the following components:

| | |
|---|---|
| PCH-3N.F.F | 10.0% by weight |
| ME3N.F | 02.0% by weight |
| ME4N.F | 03.5% by weight |
| CC-5-V | 08.0% by weight |
| CCG-V-F | 18.0% by weight |
| CCP-V-1 | 08.0% by weight |
| CCP-V2-1 | 06.0% by weight |
| CVCP-V-1 | 04.0% by weight |
| CVCP-V-O1 | 04.0% by weight |
| CVCP-1V-O1 | 05.0% by weight |
| PTP-102 | 05.0% by weight |
| PTP-201 | 03.5% by weight |
| PTP-301 | 03.0% by weight |
| PPTUI-3-2 | 10.0% by weight |
| example 86 | 10.0% by weight | wherein the acronyms have the following meaning

PCH-nN.F.F
n = 3

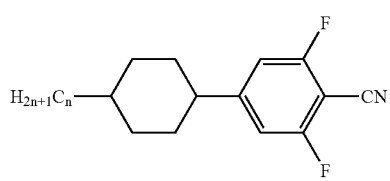

MEnN.F
n = 3 or 4

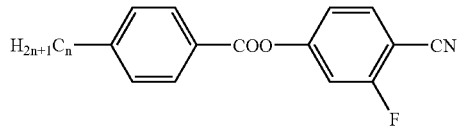

CC-n-V
n = 5

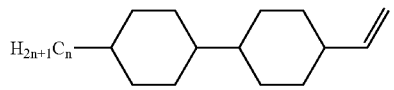

CCG-V-F

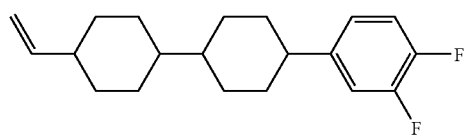

CCP-Vn-1
n = 0 or 2

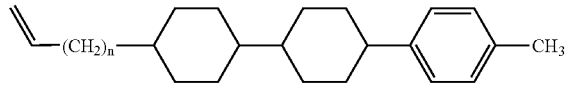

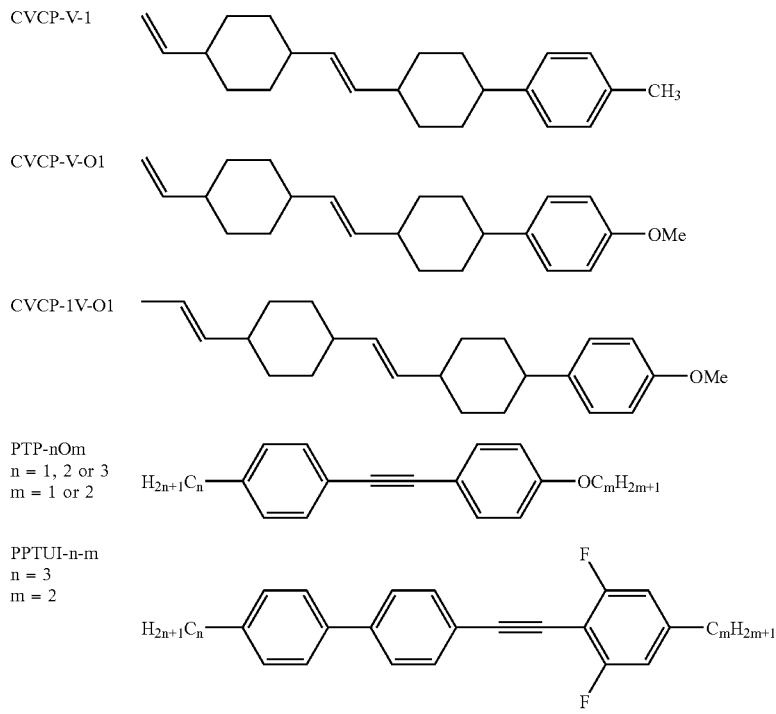

The mixture has the following properties:

| | |
|---|---|
| Clearing point: | +86.5° C. |
| Optical anisotropy Δn (589 nm, 20° C.): | +0.1629 |
| Threshold voltage $V_{10}$ (80 Hz squarewave, 20° C.): | 1.60 V |
| Steepness $V_{90}/V_{10}$ (80 Hz squarewave, 20° C.): | 1.067 |
| Average response time (duty 1/64, bias 1/9, 20° C.): | 120 ms. |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A tolane compound of the formula I

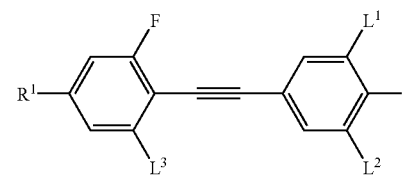

wherein
$R^1$ is an alkenyl group with 2 to 12 C-atoms,
$R^2$ is H, halogen, CN, or alkyl with 1 to 12 C-atoms, wherein one or more $CH_2$-groups are optionally replaced by —O—, —S—, —CO—, —O—CO—, —CO—O—, —CH=CH— and/or —C≡C—, and/or wherein one or more H-atoms are optionally replaced by halogen,
$L^1$, $L^2$ and $L^3$ are independently of each other H or F, with the proviso that, if $L^3$=H, then $L^1$ and $L^2$=F.

2. A tolane compound according to claim 1, which is selected from the group consisting of compounds of the sub-formulae I-1 to I-4:

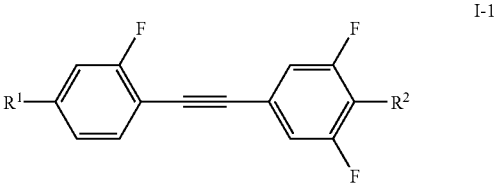

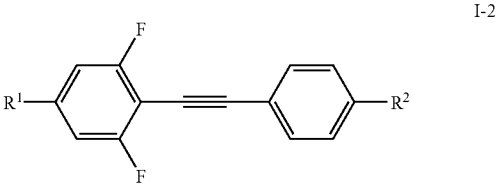

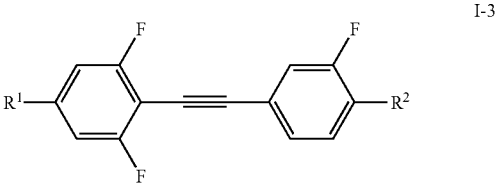

-continued

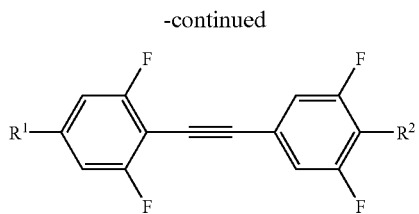

I-4 wherein $R^1$ and $R^2$ have the same meaning as defined in claim 1.

3. A tolane compound according to claim 1, wherein $R^1$ is vinyl, 1E-propenyl, 1E-butenyl, 1E-pentenyl, 1E-hexenyl, 1E-heptenyl, 1E-octenyl, 3-butenyl, 3E-pentenyl, 3E-hexenyl, 3E-heptenyl, 3E-octenyl, 4-pentenyl, 4Z-hexenyl, 4E-hexenyl, 4Z-heptenyl, 4E-octenyl, 5-hexenyl, 6-heptenyl or 7-octenyl.

4. A tolane compound according to claim 2, wherein $R^1$ is vinyl, 1E-propenyl, 1E-butenyl, 1E-pentenyl, 1E-hexenyl, 1E-heptenyl, 1E-octenyl, 3-butenyl, 3E-pentenyl, 3E-hexenyl, 3E-heptenyl, 3E-octenyl, 4-pentenyl, 4Z-hexenyl, 4E-hexenyl, 4Z-heptenyl, 4E-octenyl, 5-hexenyl, 6-heptenyl or 7-octenyl.

5. A tolane compound according to claim 1, wherein $R^2$ is —H, —F, —CN, —CHF$_2$, —CF$_3$, —OCH$_3$, —OCHF$_2$ or —OCF$_3$.

6. A tolane compound according to claim 2, wherein $R^2$ is —H, —F, —CN, —CHF$_2$, —CF$_3$, —OCH$_3$, —OCHF$_2$ or —OCF$_3$.

7. A tolane compound according to claim 3, wherein $R^2$ is —H, —F, —CN, —CHF$_2$, —CF$_3$, —OCH$_3$, —OCHF$_2$ or —OCF$_3$.

8. A tolane compound according to claim 4, wherein $R^2$ is —H, —F, —CN, —CHF$_2$, —CF$_3$, —OCH$_3$, —OCHF$_2$ or —OCF$_3$.

9. A liquid-crystalline medium having at least two liquid-crystalline components, which comprises at least one compound of the formula I as claimed in claim 1.

10. A liquid-crystalline medium having at least two liquid-crystalline components, which comprises at least one compound of the formula I as claimed in claim 2.

11. A liquid-crystalline medium having at least two liquid-crystalline components, which comprises at least one compound of the formula I as claimed in claim 3.

12. A liquid-crystalline medium having at least two liquid-crystalline components, which comprises at least one compound of the formula I as claimed in claim 5.

13. A liquid-crystal display element, which contains a liquid-crystalline medium according to claim 9.

14. A liquid-crystal display element, which contains a liquid-crystalline medium according to claim 10.

15. A liquid-crystal display element, which contains a liquid-crystalline medium according to claim 11.

16. A liquid-crystal display element, which contains a liquid-crystalline medium according to claim 12.

17. An Electro-optical display element, which contains a liquid-crystalline medium according to claim 9.

18. An Electro-optical display element, which contains a liquid-crystalline medium according to claim 10.

19. An Electro-optical display element, which contains a liquid-crystalline medium according to claim 11.

20. An Electro-optical display element, which contains a liquid-crystalline medium according to claim 12.

* * * * *